(12) United States Patent
Mizuno

(10) Patent No.: US 11,890,110 B2
(45) Date of Patent: Feb. 6, 2024

(54) ELECTRONIC DEVICE, METHOD AND STORAGE MEDIUM

(71) Applicant: CASIO COMPUTER CO., LTD., Tokyo (JP)

(72) Inventor: Kimiyasu Mizuno, Akishima (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 213 days.

(21) Appl. No.: 17/104,701

(22) Filed: Nov. 25, 2020

(65) Prior Publication Data

US 2021/0161468 A1 Jun. 3, 2021

(30) Foreign Application Priority Data

Nov. 29, 2019 (JP) ................................. 2019-216389

(51) Int. Cl.
*A61B 5/00* (2006.01)
*A61B 5/024* (2006.01)
(Continued)

(52) U.S. Cl.
CPC .......... *A61B 5/681* (2013.01); *A61B 5/02438* (2013.01); *G04G 21/025* (2013.01); *G06F 1/163* (2013.01); *G16H 40/67* (2018.01)

(58) Field of Classification Search
CPC .. A61B 5/681; A61B 5/02438; G04G 21/025; G16H 40/67; G06F 1/163
(Continued)

(56) References Cited

U.S. PATENT DOCUMENTS 10,098,572 B2 * 10/2018 Schwenk ............... A61B 5/721
2010/0331145 A1 * 12/2010 Lakovic ................. G04G 21/02
482/8
(Continued)

FOREIGN PATENT DOCUMENTS

CN 106510676 B * 10/2019 ........... A61B 5/0205
EP 1894521 A1 * 3/2008 ......... A61B 5/02438
(Continued)

OTHER PUBLICATIONS

JPO; Application No. 2019-216389; Notice of Reasons for Refusal dated Nov. 24, 2021.
(Continued)

*Primary Examiner* — Carl H Layno
*Assistant Examiner* — Michael J Lau
(74) *Attorney, Agent, or Firm* — Fitch, Even, Tabin & Flannery LLP

(57) ABSTRACT

An electronic device includes a biological information acquirer that acquires biological information of a target; an error factor detector that detects a factor that causes an error in the biological information; a display; and at least one processor. The error factor detector includes a motion detection sensor that detects a direction of motion of the electronic device, and the processor is that determines whether the factor is detected, based on the direction of the motion of the electronic device; and to cause, when the processor determines that the factor is detected, the display not to display the biological information acquired by the biological information acquirer, or to cause the biological information acquirer to stop acquisition of the biological information, in a period determined based on a timing when the factor is detected.

10 Claims, 8 Drawing Sheets

(51) Int. Cl.
  *G04G 21/02* (2010.01)
  *G06F 1/16* (2006.01)
  *G16H 40/67* (2018.01)
(58) Field of Classification Search
  USPC ........................................................ 600/301
  See application file for complete search history.

(56) References Cited

U.S. PATENT DOCUMENTS

| | | | |
|---|---|---|---|
| 2012/0123226 A1* | 5/2012 | Schwenk | A61B 5/1123 600/595 |
| 2019/0018506 A1* | 1/2019 | Bernstein | G06F 3/0487 |
| 2019/0117092 A1 | 4/2019 | Yamashita et al. | |
| 2019/0268771 A1* | 8/2019 | Seo | H04W 12/33 |

FOREIGN PATENT DOCUMENTS

| | | | | |
|---|---|---|---|---|
| JP | H8-317912 A | | 12/1996 | |
| JP | 2005-095653 A | | 4/2005 | |
| JP | 2005095653 A | * | 4/2005 | ............. A61B 5/024 |
| JP | 2016-198554 A | | 12/2016 | |
| JP | 2016198554 A | * | 12/2016 | ......... A61B 5/02427 |
| JP | 2017-225756 A | | 12/2017 | |
| JP | 2017225756 A | * | 12/2017 | ............... A61B 5/02 |
| JP | 2018-007887 A | | 1/2018 | |
| WO | WO-2011010244 A1 | * | 1/2011 | ........... A61B 5/1118 |

OTHER PUBLICATIONS

CNIPA; Application No. 202011357614.7; Office Action dated May 11, 2023.

\* cited by examiner

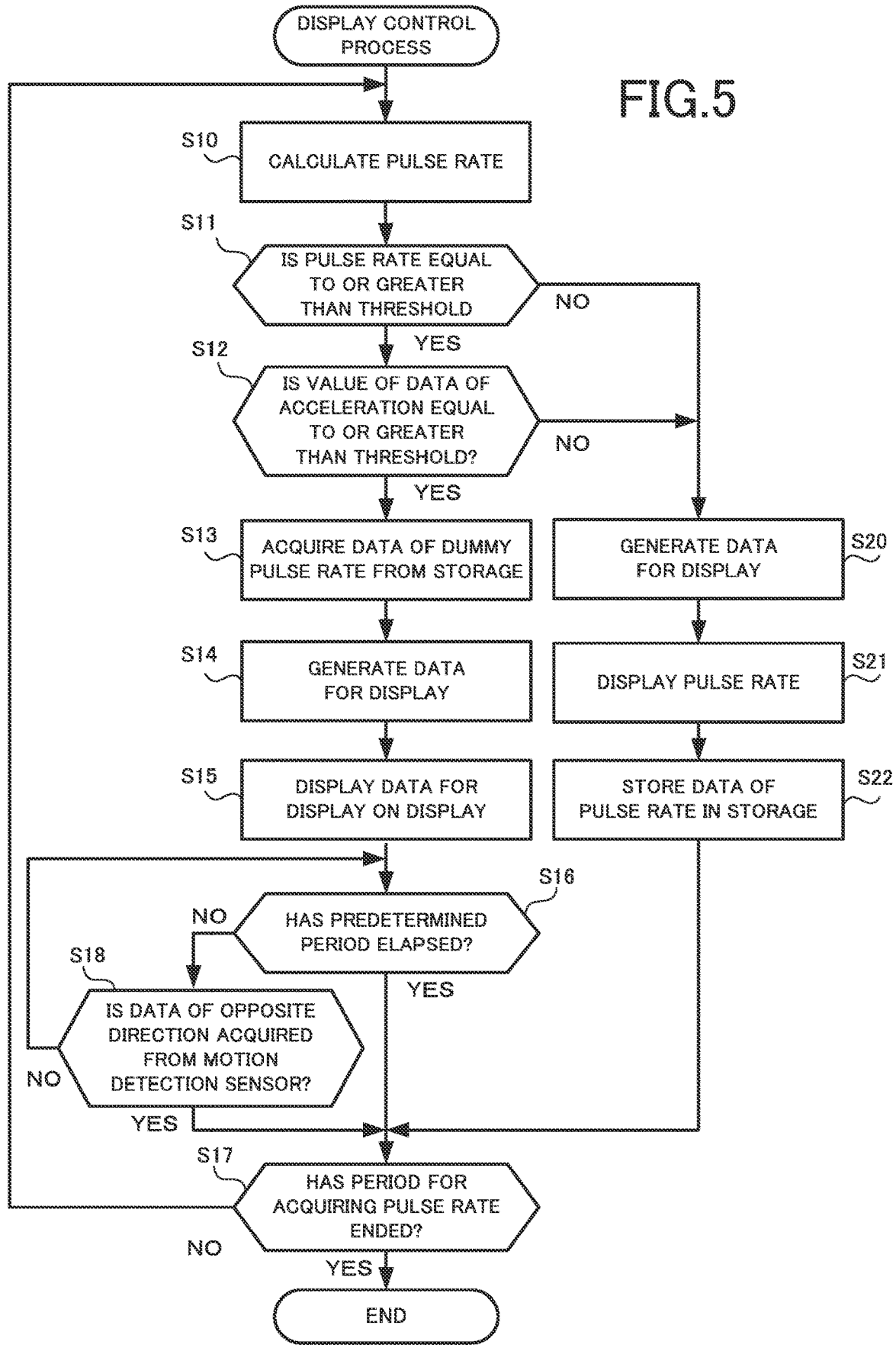

ELECTRONIC DEVICE, METHOD AND STORAGE MEDIUM

CROSS-REFERENCE TO RELATED APPLICATION

This application claims the benefit of Japanese Patent Application No. 2019-216389, filed on Nov. 29, 2019, the entire disclosure of which is incorporated by reference herein.

FIELD

This application relates generally to an electronic device which measures and displays biological information of a user such as a pulse rate, a method, and a storage medium.

BACKGROUND

For example, Unexamined Japanese Patent Application Publication No. 2018-007887 discloses an electronic device which is worn on a wrist, and measures and displays the pulse rate.

SUMMARY

The present embodiment is an electronic device including:
a biological information acquirer that acquires biological information of a target;
an error factor detector that detects a factor that cases an error in the biological information;
a display; and
at least one processor, wherein
the error factor detector includes a motion detection sensor that detects a direction of motion of the electronic device, and
the processor
determines whether the factor is detected, based on the direction of the motion of the electronic device; and
causes, when the processor determines that the factor is detected, the display not to display the biological information acquired by the biological information acquirer, or cause the biological information acquirer to stop acquisition of the biological information, in a first period determined based on a timing when the factor is detected, and
causes, when the processor determines that the factor is not detected, the display to display the biological information acquired by the biological information acquirer.

BRIEF DESCRIPTION OF THE DRAWINGS

A more complete understanding of this application can be obtained when the following detailed description is considered in conjunction with the following drawings, in which:

FIG. 5 is a flowchart illustrating a flow of a display control process which is executed by the electronic device according to Embodiment 1.

DETAILED DESCRIPTION

Figure 1A:
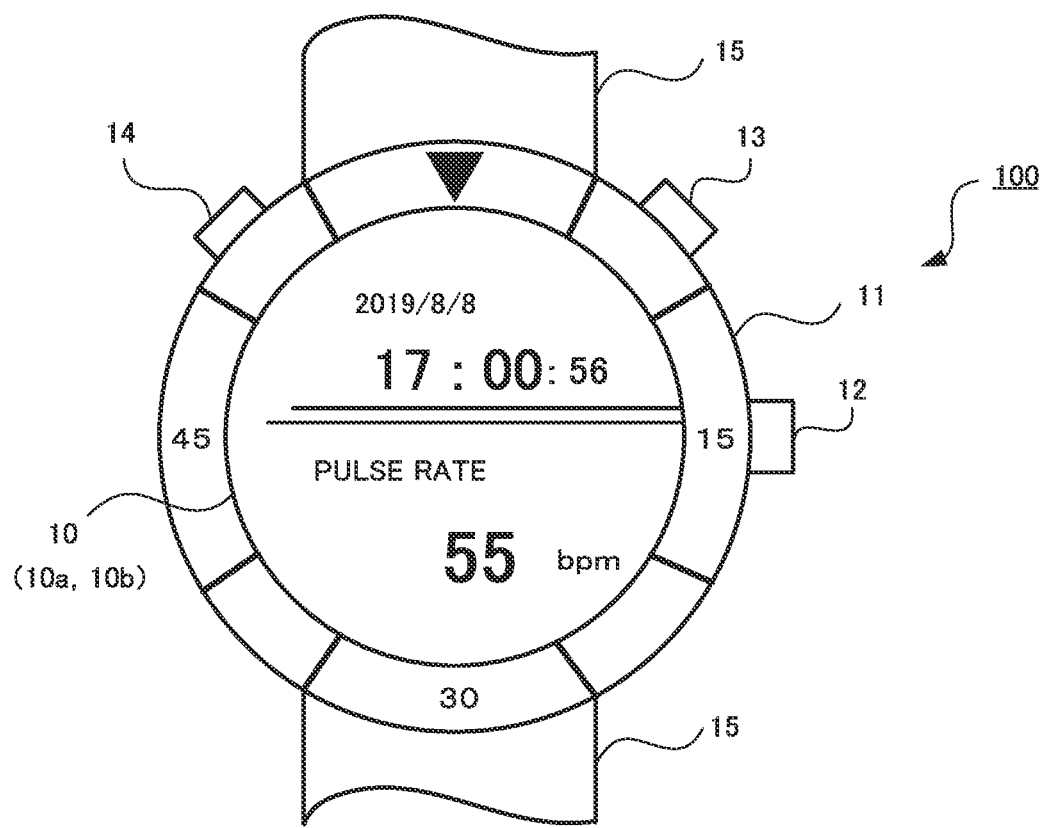
FIG. 1A is a view illustrating a front surface of an electronic device according to Embodiment 1.

Hereinafter, the present embodiments will be described in detail with reference to the accompanying drawings. Note that identical or corresponding parts in the drawings are denoted by identical reference signs.

Embodiment 1

An electronic device 100 according to Embodiment 1 is a so-called wearable terminal, and is a device which can display time and date, a pulse rate of a user who wears the electronic device 100, and the like. Hereinafter, a description will be given by taking a pulse rate as an example of biological information of the user. FIG. 1A illustrates a front surface of the electronic device 100, the front surface being a surface which the user views when the electronic device 100 is worn. The electronic device 100 includes a display 10 which displays time and date, a pulse rate, and the like; a rotary bezel 11 which is rotatable; a crown 12 for adjusting time; push buttons 13 and 14 for various settings; and a belt 15 for attaching the electronic device 100 to the user. The display 10 includes a display device 10*a* and a touch panel 10*b* functioning as an operation inputter. Note that the user who wears the electronic device 100 is an example of a target in the patent claims.

In Embodiment 1, as illustrated in FIG. 1A, it is assumed that the display 10 displays the present time and date and the pulse rate. Note that one of the present time and date and the pulse rate may be displayed, and the displayed screen may be switched by an operation from the push buttons 13, 14, touch panel 10*b*, or the like. In addition, a screen displaying both the present time and date and the pulse rate and a screen displaying one of the present time and date and the pulse rate may be switched by an operation from the push button 13, 14, touch panel 10*b*, or the like.

Figure 1B:
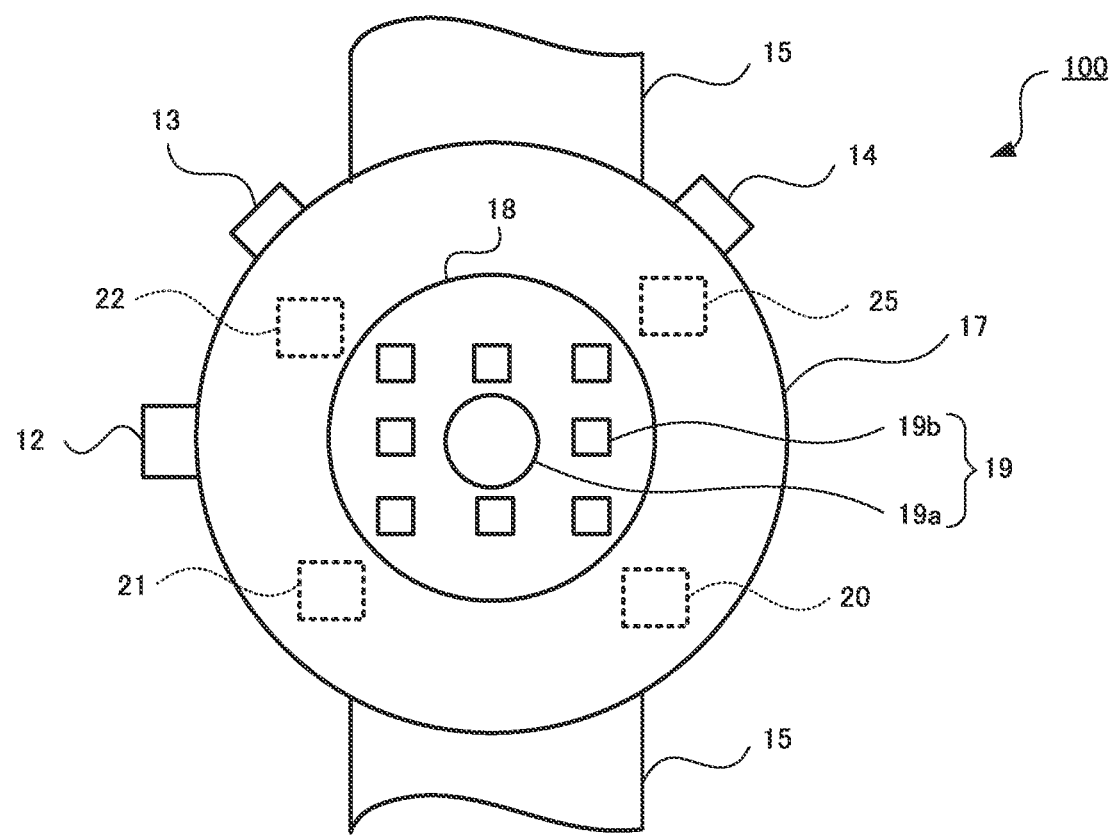
FIG. 1B is a view illustrating a back surface of the electronic device according to Embodiment 1.

FIG. 1B illustrates a back surface of the electronic device 100, the back surface being a surface which is put in contact with the user when the electronic device 100 is worn. The back surface of the electronic device 100 includes a back-surface cover 17, a glass window 18 which transmits light, and a pulse sensor 19. The pulse sensor 19 includes a light transmitter 19*a* and a plurality of light receivers 19*b*. Light emitted from the light emitter 19*a* of the pulse sensor 19 passes through the glass window 18, and is radiated on the wrist, upper arm or the like of the user who wears the electronic device 100. The radiated light is reflected by a blood vessel, made incident on the glass window 18, and received by the light receivers 19*b*.

Blood includes oxyhemoglobin with such properties as to absorb light. When the light emitted from the light emitter 19*a* is radiated on the blood vessel, part of the light is absorbed in the blood. Thus, the light quantity of reflective light from the blood vessel varies in accordance with a blood flow rate which varies in accordance with the pulsation of the heart. Hence, the pulse of the user can be detected by receiving the reflective light from the blood vessel by the light receivers 19*b*.

In addition, the electronic device 100 includes therein a motion detection sensor 20 which detects motion of the user wearing the electronic device 100; a storage 21 which stores various data, programs, and the like; a clock 22 which measures time; and a controller 25 which controls various functions that are executed by the electronic device 100.

Figure 2:
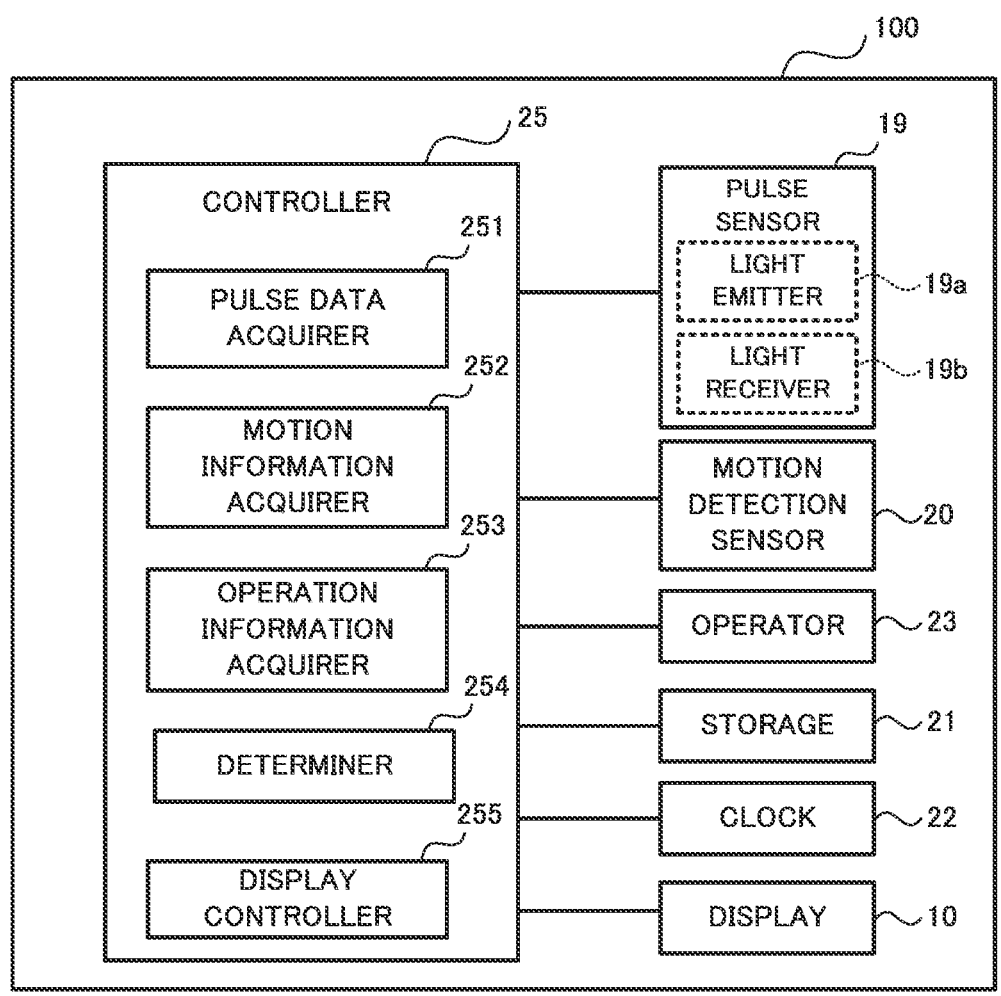
FIG. 2 is a circuit block diagram of the electronic device according to Embodiment 1.

Next, circuit blocks of the electronic device 100 will be described. As illustrated in FIG. 2, the electronic device 100 includes the pulse sensor 19 which detects the pulse data of the user; the motion detection sensor 20 which detects acceleration and a direction of motion; an operator 23 which accepts an operation from the user; the storage 21 which stores various data and programs; the clock 22 which measures time; the display 10 which effects display by display control from the controller 25; and the controller 25.

The light emitter 19*a* of the pulse sensor 19 can be constituted by a light emitting diode (LED) which can radiate light such as infrared, red light, or the like. In addition, the light receivers 19*b* can be constituted by using, for example, light receiving elements such as photodiodes, phototransistors, or the like. The motion detection sensor 20 can judge the motion of an action of the user who wears the electronic device 100, based on the detected acceleration and the direction of movement of the electronic device 100. The motion detection sensor 20 can be constituted by, for example, a gyro sensor, an acceleration sensor, or the like.

The operator 23 is a function of accepting an operation from the user. Hereinafter, the rotary bezel 11, crown 12, push buttons 13 and 14, and touch panel 10*b* are comprehensively referred to as the operator 23. The storage 21 is a memory device which stores various data, programs, and the like, and can be constituted by, for example, a nonvolatile memory element such as a read-only memory (ROM), a flash memory, or the like.

The clock 22 measures time, for example, by using a reference signal by an oscillation signal of a quartz oscillator or the like. The time measured by the clock 22 is displayed on the display 10 illustrated in FIG. 1A. The display 10 includes a display device 10*a* and a touch panel 10*b* that is an operation inputter. The display device 10*a* is a display device such as a liquid crystal display (LCD), a plasma display panel (PDP), an organic electro-luminescence (EL) display device, or the like, and the display device 10*a* displays various images, characters, signs and the like according to control by the controller 25 (to be described later). The touch panel 10*b* is a touch panel of a resistive type, a capacitive type or the like, which detects a position touched by the user and outputs the detected position to the controller 25 (to be described later).

The controller 25 controls various functions which are executed by the electronic device 100. The controller 25 includes a central processing unit (CPU) which executes programs stored in the storage 21, a random-access memory (RAM) for reading in the programs stored in the storage 21, an interface for acquiring various data from the pulse sensor 19, the motion detection sensor 20 and the operator 23, and a graphic processing unit (GPU) for display control.

By executing the programs stored in the storage 21, the controller 25 functions as a pulse data acquirer 251 which acquires pulse data of the user; a motion information acquirer 252 which acquires information relating to the motion of the user; an operation information acquirer 253 which acquires information relating to an operation from the user; a determiner 254; and a display controller 255 which controls display of the display 10.

The pulse data acquirer 251 acquires the pulse data of the user wearing the electronic device 100 from the pulse sensor 19, and calculates a pulse rate from the acquired pulse data of the user. The motion information acquirer 252 acquires data of acceleration and data of a direction of motion of the electronic device 100 from the motion detection sensor 20. The operation information acquirer 253 acquires data relating to an operation from the user, which is detected by the operator 23. Based on the pulse rate calculated by the pulse data acquirer 251, and the data acquired by the motion information acquirer 252 and operation information acquirer 253, the determiner 254 determines whether or not to display the pulse rate, which is calculated from the pulse data acquired by the pulse data acquirer 251, as such on the display 10, as the pulse rate that is to be displayed on the display 10. The determination in the determiner 254 will be described later in detail. The display controller 255 generates display data that is to be displayed on the display 10, in accordance with the determination result of the determiner 254, and causes the display 10 to display the display data. Note that the determiner 254 is an example of determination means in the patent claims. In addition, the display controller 255 is an example of a display controller in the patent claims. Besides, the user is an example of a target in the patent claims.

In the electronic device 100, as described above, the pulse of the user wearing the electronic device 100 is detected by the pulse sensor 19, and the pulse rate calculated from the detected pulse data can be displayed on the display 10. In the pulse sensor 19, the light emitted from the light emitter 19*a* is radiated on the blood vessel of the user, and reflective light from the blood vessel is received by the light receivers 19*b*. The reflective light from the blood vessel, which is received by the light receivers 19*b*, varies in accordance with the blood flow of the user.

Figure 3:
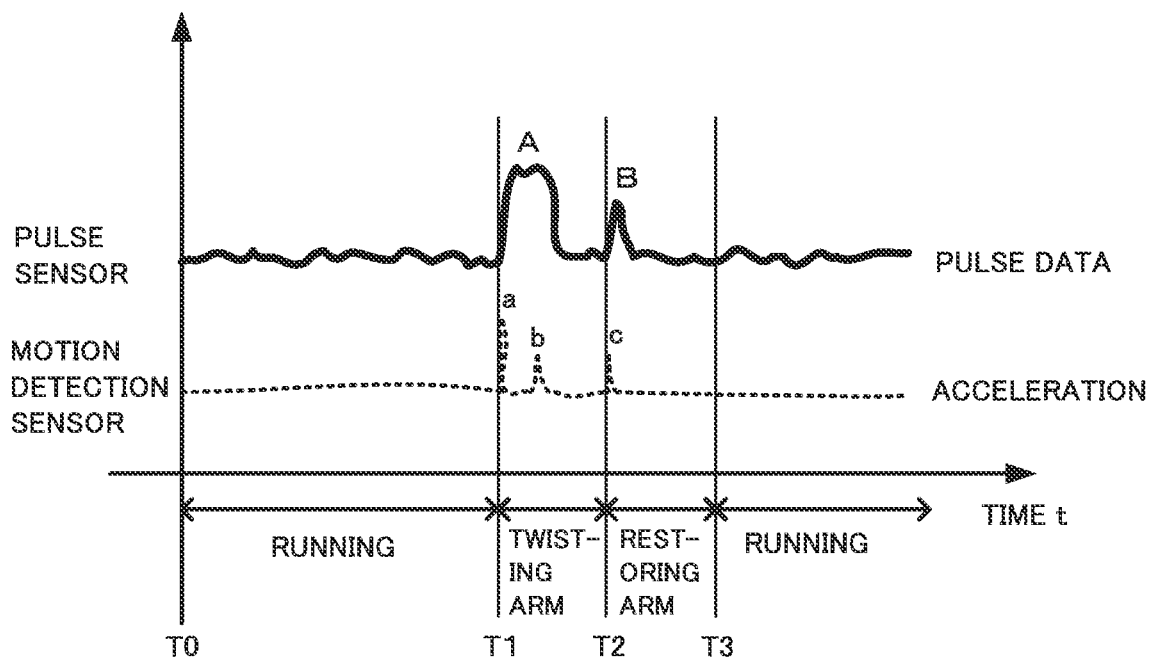
FIG. 3 is a view illustrating an example of a variation of a pulse rate which is measured in the electronic device according to Embodiment 1.

For example, as illustrated in FIG. 3, when the user wearing the electronic device 100 is running, no great variation occurs in the value of the pulse data detected by the pulse sensor 19 during a period from time T0 to time T1. Thus, during the period from time T1 to time T1, the pulse rate that is displayed on the display 10 of the electronic device 100 is substantially constant. In addition, as illustrated in FIG. 3, during the period from time T0 to time T1 in which the user is running, the value of the pulse data detected by the motion detection sensor 20 is a value that does not greatly vary.

Then, at time T1, for example, it is assumed that the user twists the arm in order to confirm the present time, and moves the electronic device 100 to the front of the eyes. In this case, since the amount of blood flowing in the blood vessel greatly varies in accordance with the twist of the arm, the value detected by the pulse sensor 19 becomes greater than the value detected before, as indicated by a waveform A in FIG. 3. Thereafter, if the state in which the arm is twisted continues, since the amount of blood flowing in the blood vessel does not greatly vary, the value of the pulse data detected by the pulse sensor 19 becomes closer to the value at the time before time T1 at which the arm was twisted.

In addition, at time T1, immediately after the user twists the arm, the value of data of acceleration, which is detected by the motion detection sensor 20, becomes a greater value than while the user is running, as indicated by a waveform a. Then, if the user does not move, the value of data of acceleration, which is detected by the motion detection sensor 20, becomes equal to the value detected while the user is running. Subsequently, when the user further moves the arm, for example, by moving the display 10 of the electronic device 100 to an easier-to-view position, the motion detection sensor 20 detects data of acceleration, which has a greater value than while the user is running, as indicated by a waveform b.

Thereafter, at time T2, for example, it is assumed that the user ends the confirmation of the present time, and restores the arm to the position before twisting the arm, that is, to the position while the user is running. In this case, the amount of blood flowing in the blood vessel greatly varies in accordance with the motion of restoring the arm. Thus, the value of the pulse data detected by the pulse sensor 19 becomes greater than the value detected before, as indicated by a waveform B in FIG. 3. Thereafter, if the state in which the arm is restored continues, the amount of blood flowing in the blood vessel does not greatly vary. Thus, the value of the pulse data detected by the pulse sensor 19 becomes closer to the value at the time before time T1 at which the arm was twisted. After time T3, if the user does not move the arm, such as by twisting and restoring the arm, no great variation occurs in the value of pulse data detected by the pulse sensor 19.

In addition, when the user ends the confirmation of the present time and restores the arm to the position before twisting the arm, that is, to the position while the user is running, the motion detection sensor 20 detects the value of data of acceleration, which has a greater value than while the user is running, as indicated by a waveform c. Then, if no motion occurs, the value of data of acceleration, which is detected by the motion detection sensor 20, becomes equal to the value detected while the user is running. After time T3, if the user does not move the arm, such as by twisting and restoring the arm, no great variation occurs in the value of data of acceleration detected by the motion detection sensor 20. Note that the direction of motion of the electronic device 100, which is detected by the motion detection sensor 20 when the arm is twisted at time T1, is opposite to the direction of motion of the electronic device 100, which is detected by the motion detection sensor 20 when the arm is restored at time T2.

In this manner, when the user twists the arm and then restores the arm, the value detected by the pulse sensor 19 greatly varies only immediately after the motion of twisting the arm and the motion of restoring the arm. The value of pulse data detected by the pulse sensor 19 in this case is not a value which is to be normally detected, but a value including an error occurring in accordance with the motion. When the pulse rate generated based on the pulse data including the error is displayed on the display 10 of the electronic device 100, the user will view the pulse rate including the error.

However, as described above, if the amount of blood flowing in the blood vessel does not greatly vary in the state in which the arm is twisted and in the state in which the arm is restored, the pulse data detected by the pulse sensor 19 becomes substantially equal to the value immediately before the motion of twisting the arm and the motion of restoring the arm. The value of pulse data detected by the pulse sensor 19 in this case is a value which is to be normally detected, and a value including no error which occurs in accordance with the motion. Thus, there is a possibility that, shortly after the user views the pulse rate including an error on the screen of the display 10, the user views the pulse rate including no error. It is thus possible that the user doubts whether the displayed pulse rate is correct or not.

When the pulse data detected by the pulse sensor 19 includes an error, the motion detection sensor 20 also detects data of acceleration having a greater value than while the user is running, as described above. Specifically, the motion detection sensor 20 can detect data of acceleration, which is a factor of the error included in the pulse data. Thus, in Embodiment 1, when a pulse rate calculated from pulse data detected by the pulse sensor 19 is equal to or greater than a threshold, an acceleration by motion of a user and a direction of the motion are detected by the motion detection sensor 20, and when the determiner 254 of the controller 25 illustrated in FIG. 2 determines that a motion that is an error factor is performed, based on the detected acceleration, a pulse rate including no error is displayed in place of a pulse rate including an error. Hereinafter, the pulse rate including no error, which is displayed in place of the pulse rate including an error, is referred to as "dummy pulse rate".

In Embodiment 1, as the dummy pulse rate, use is made of the pulse rate calculated from the pulse data that was detected by the pulse sensor 19 immediately before, for example, time T1 or time T2 illustrated in FIG. 3, that is, a pulse rate immediately before the user performs a motion that is an error factor. Thereby, the pulse rate displayed on the display 10 of the electronic device 100 does not greatly vary, and the possibility lowers that the user doubts whether the displayed pulse rate is correct or not.

Figure 4A:
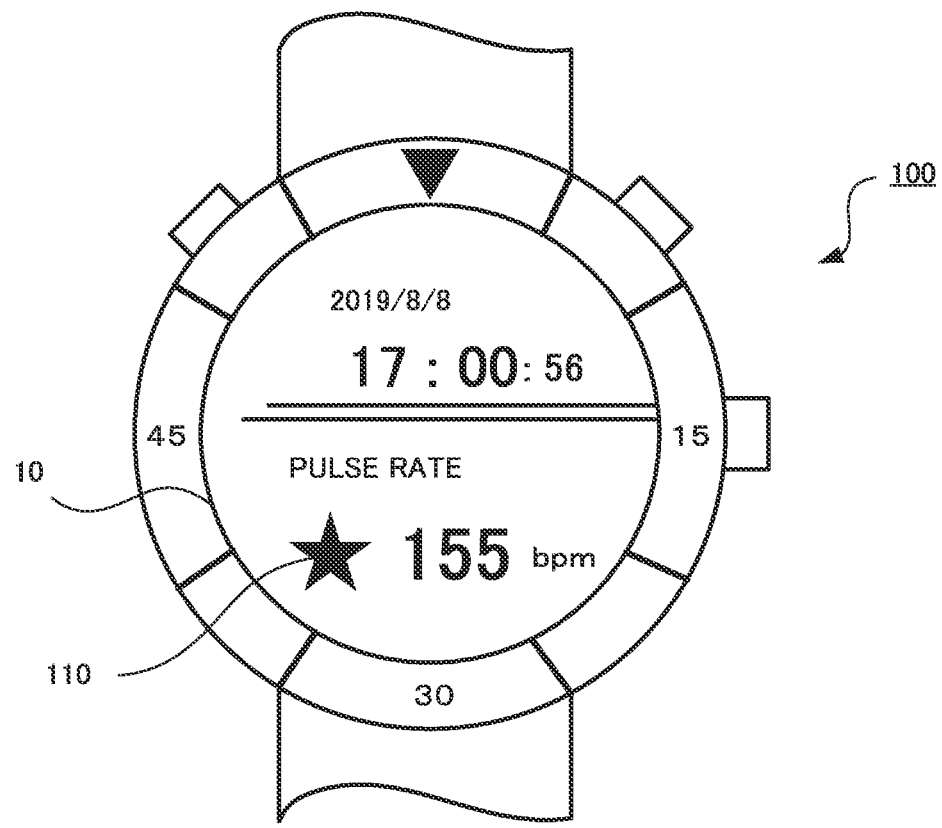
FIG. 4A and FIG. 4B are views illustrating examples of display of a pulse rate at a time when an error occurs in the electronic device according to Embodiment 1.
Figure 4B:
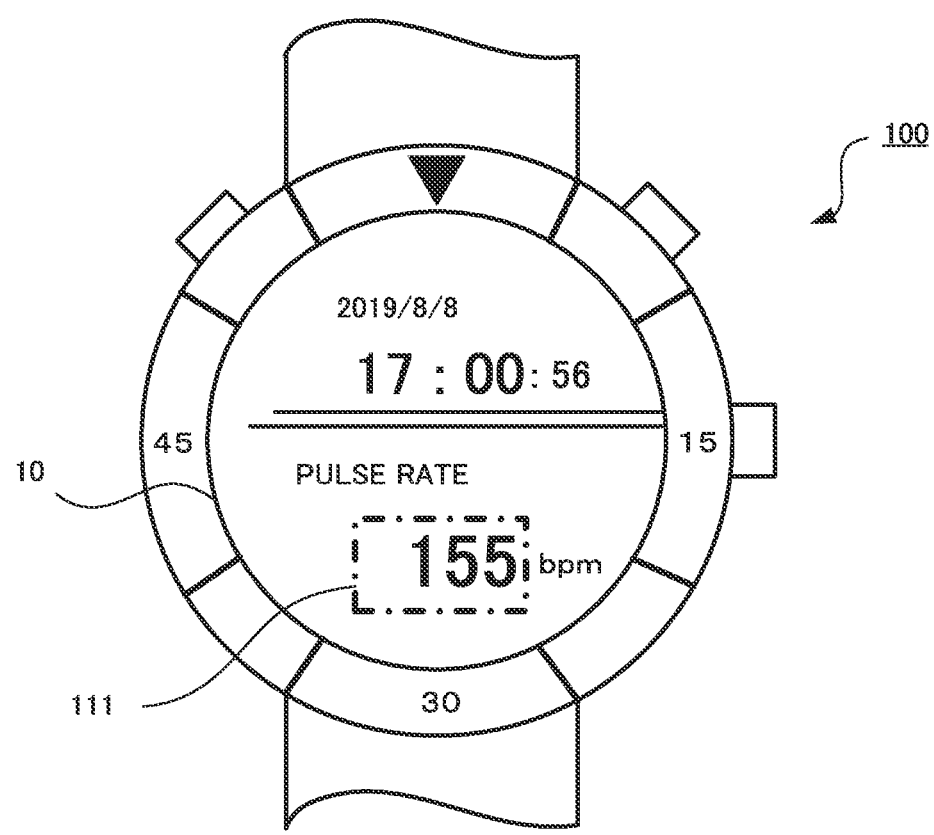

In addition, when the dummy pulse rate is displayed on the display 10 illustrated in FIG. 1, the display mode is made different between the dummy pulse rate and the pulse rate calculated from the data acquired from the pulse sensor 19. Thereby, the user is enabled to understand that the dummy pulse rate is displayed. For example, as illustrated in FIG. 4A, a specific mark 110 is displayed near the display of the pulse rate, or, as illustrated in FIG. 4B, a frame 111 surrounding the display of the pulse rate is displayed, or the color of characters displaying the pulse rate is made different from the color for normal display. The specific mark 110, frame 111, the color of characters, and the like, are stored in the storage 21 illustrated in FIG. 2 as set data for dummy display.

Referring to a flowchart of a display control process illustrated in FIG. 5, a description will be given of the control to display, in the electronic device 100, a pulse rate including no error in place of a pulse rate including an error. The display control process is stored as a display control process program in the storage 21 illustrated in FIG. 2. In the electronic device 100, when the function of measuring the pulse rate of the user and displaying the pulse rate is executed, the controller 25 illustrated in FIG. 2 reads out the display control process program from the storage 21, loads the display control process program in the RAM of the controller 25, and executes the display control process program.

The pulse data acquirer 251 of the controller 25 illustrated in FIG. 2 acquires pulse data of the user from the pulse sensor 19. The pulse data acquirer 251 calculates a pulse rate from the acquired pulse data (step S10). The determiner 254 of the controller 25 acquires the pulse rate of the user from the pulse data acquirer 251, and determines whether or not the pulse rate is equal to or greater than a threshold (step S11). When the pulse rate is equal to or greater than the threshold (step S11; YES), the motion information acquirer 252 of the controller 25 illustrated in FIG. 2 acquires data of acceleration detected from the motion detection sensor 20. In addition, the motion information acquirer 252 acquires data of a direction of motion of the electronic device 100 from the motion detection sensor 20, the direction of motion being detected by the motion detection sensor 20. Here, it is assumed that the user twists the arm on which the electronic device 100 is worn, for example, at time T1 illustrated in FIG. 3.

The determiner 254 determines whether the value of the data of acceleration acquired by the motion information acquirer 252 is equal to or greater than a threshold (step S12). When the determiner 254 determines whether the value of the data of acceleration is equal to or greater than the threshold (step S12; YES), the display controller 255 acquires data of the pulse rate, which was stored immediately before and includes no error, from the storage 21, that is, data of a dummy pulse rate (step S13). Subsequently, the display controller 255 acquires set data for dummy display from the storage 21. The display controller 255 generates data for display, based on the data of the dummy pulse rate and the acquired set data for dummy display (step S14). For example, as illustrated in FIG. 4A, the display controller 255 generates data for display, which displays the specific mark 110 near the display of the pulse rate.

The display controller 255 causes the display 10 illustrated in FIG. 1 to display the generated data for display (step S15). Thereby, the display controller 255 updates display content that is displayed on the display 10. The determiner 254 determines whether or not a predetermined period has elapsed since the data for display generated by the display controller 255 was displayed on the display 10 (step S16). The predetermined period is, for example, a period preset by the user, or a period determined based on a timing when a factor of an error was detected, or the like. When the determiner 254 determines that the predetermined period has elapsed (step S16; YES), the determiner 254 determines whether a period for acquiring a pulse rate has terminated (step S17). For example, by an operation from the push button 13, 14, or the touch panel 10b, illustrated in FIG. 1, when the screen is switched from the screen displaying both the present time and the pulse rate to the screen displaying only the present time, or when an instruction not to acquire the pulse rate is given, the determiner 254 can determine that the period for acquiring the pulse rate has ended.

When the determiner 254 determines that the period for acquiring the pulse rate has ended (step S17; YES), the controller 25 terminates the display control process program. On the other hand, when the determiner 254 does not determine that the period for acquiring the pulse rate has ended (step S17; NO), the controller 25 returns to step S10 and executes step S10 onwards.

In step S16, when the determiner 254 does not determine that the predetermined period has elapsed (step S16; NO), the motion information acquirer 252 of the controller 25 illustrated in FIG. 2 acquires the data of the direction of motion of the electronic device 100 from the motion detection sensor 20. The determiner 254 determines whether the acquired data of the direction of motion of the electronic device 100 and the data of the direction of motion of the electronic device 100, which was acquired by the motion information acquirer 252 before the determination in step S12, are the data of opposite directions (step S18).

Here, it is assumed that the user restored the state of the arm wearing the electronic device 100 from the state in which the arm is twisted to the state before twisting the arm, that is, to the state at the time when the user is running, for example, at time T2 illustrated in FIG. 3. In this case, the data of the direction of motion of the electronic device 100, which is acquired by the motion information acquirer 252 from the motion detection sensor 20, is the data of the opposite direction to the data of the direction of motion of the electronic device 100, which was acquired before the determination in step S12. Thus, the determiner 254 determines that the data of the opposite direction is acquired (step S18; YES), and the controller 25 executes step S17. On the other hand, if the determiner 254 determines that the data of the opposite direction is not acquired (step S18; NO), the controller 25 returns to step S16 and executes step S16 onwards.

In addition, if the determiner 254 determines in step S11 that the pulse rate, which is calculated from the pulse data acquired by the pulse data acquirer 251 of the controller 25, is not equal to or greater than the threshold (step S11; NO), or if the determiner 254 determines in step S12 that the value of the data of acceleration acquired by the motion detection sensor 20 is not equal to or greater than the threshold (step S12; NO), the display controller 255 generates data for display, based on the pulse rate calculated from the pulse data of the user acquired from the pulse data acquirer 251 (step S20). The display controller 255 causes the display 10 illustrated in FIG. 1 to display the generated data for display (step S21). Thereby, the display controller 255 updates the display content that is displayed on the display 10. The pulse data acquirer 251 stores the pulse rate calculated from the pulse data acquired from the pulse sensor 19 in the storage 21 (step S22). The controller 25 executes step S17.

As described above, according to the electronic device 100 of Embodiment 1, the acceleration by motion of the user and the direction of the motion are detected by the motion detection sensor 20. Thereby, in the electronic device 100 that is worn, the pulse rate including no error due to the motion of the user, that is, the biological information including no error, can be displayed. Hence, a great variation does not occur in the value of the biological information displayed on the display 10 of the electronic device 100, and the possibility can be lowered that the user doubts whether the value of the displayed biological information is correct or not. In Embodiment 1, it is assumed that the acceleration by motion of the user and the direction of the motion are detected by the motion detection sensor 20, but Embodiment 1 is not limited to this. For example, the twisting of the arm may be detected by detecting only the acceleration by motion of the user. Besides, the twisting of the arm may be detected by detecting only the direction of motion of the user.

Embodiment 2

In Embodiment 1 described above, when the pulse rate, which is calculated from the pulse data detected by the pulse sensor 19, is equal to or greater than the threshold, it is determined whether the dummy pulse rate is to be displayed on the display 10 of the electronic device 100, in accordance with the value of data of acceleration by motion of the user, the acceleration being acquired from the motion detection sensor 20. The reason for this is that, for example, immediately after the motion of twisting the arm wearing the electronic device 100 and the motion of restoring the twisted arm, the blood flow in the blood vessel of the arm varies, and thus the value of the pulse data detected by the pulse sensor 19 includes an error.

However, the blood flow in the blood vessel of the arm also varies in motion other than the motion of twisting and restoring the arm. For example, when the rotary bezel 11 of the electronic device 100 illustrated in FIG. 1A is rotated, the user rotates the rotary bezel 11 in the state in which the electronic device 100 is pushed and fixed on the arm. While the electronic device 100 is pushed on the arm by the user, the blood vessel is pressed and, therefore, the blood flow in the blood vessel varies.

In addition, also when the crown 12, or the push button 13, 14, illustrated in FIG. 1A, is operated, the user operates the crown 12, or the push button 13, 14, in the state in which the electronic device 100 is pushed and fixed on the arm, like the case of rotating the rotary bezel 11. Further, when the user operates the touch panel 10b of the display 10, a pressure acts on the touch panel 10b by the finger of the user, and, as a result, the electronic device 100 is pushed on the arm. Thus, since the blood vessel is pressed also when such operations are performed, the blood flow in the blood vessel varies.

As described above, when an operation from the user is performed on the operator 23 illustrated in FIG. 2, which includes the rotary bezel 11, the crown 12, the push buttons 13 and 14 and the touch panel 10b illustrated in FIG. 1A, the blood vessel of the arm is pressed and the blood flow in the blood vessel varies. Consequently, there is a possibility that the pulse data detected by the pulse sensor 19 includes an error. Thus, by detecting that an operation by the user is performed on the operator 23, a factor of the error included in the pulse data can be detected.

Thus, in Embodiment 2, when the pulse rate, which is calculated from the pulse data detected by the pulse sensor 19, is equal to or greater than the threshold, it is determined whether or not to cause the display 10 of the electronic device 100 to display the dummy pulse rate, according to whether an operation from the user is accepted by the operator 23 illustrated in FIG. 2, which includes the rotary bezel 11, crown 12, push buttons 13 and 14 and touch panel 10b illustrated in FIG. 1A. Note that the motion detection sensor 20 and the operator 23 are an example of an error factor detector in the patent claims.

Figure 6:
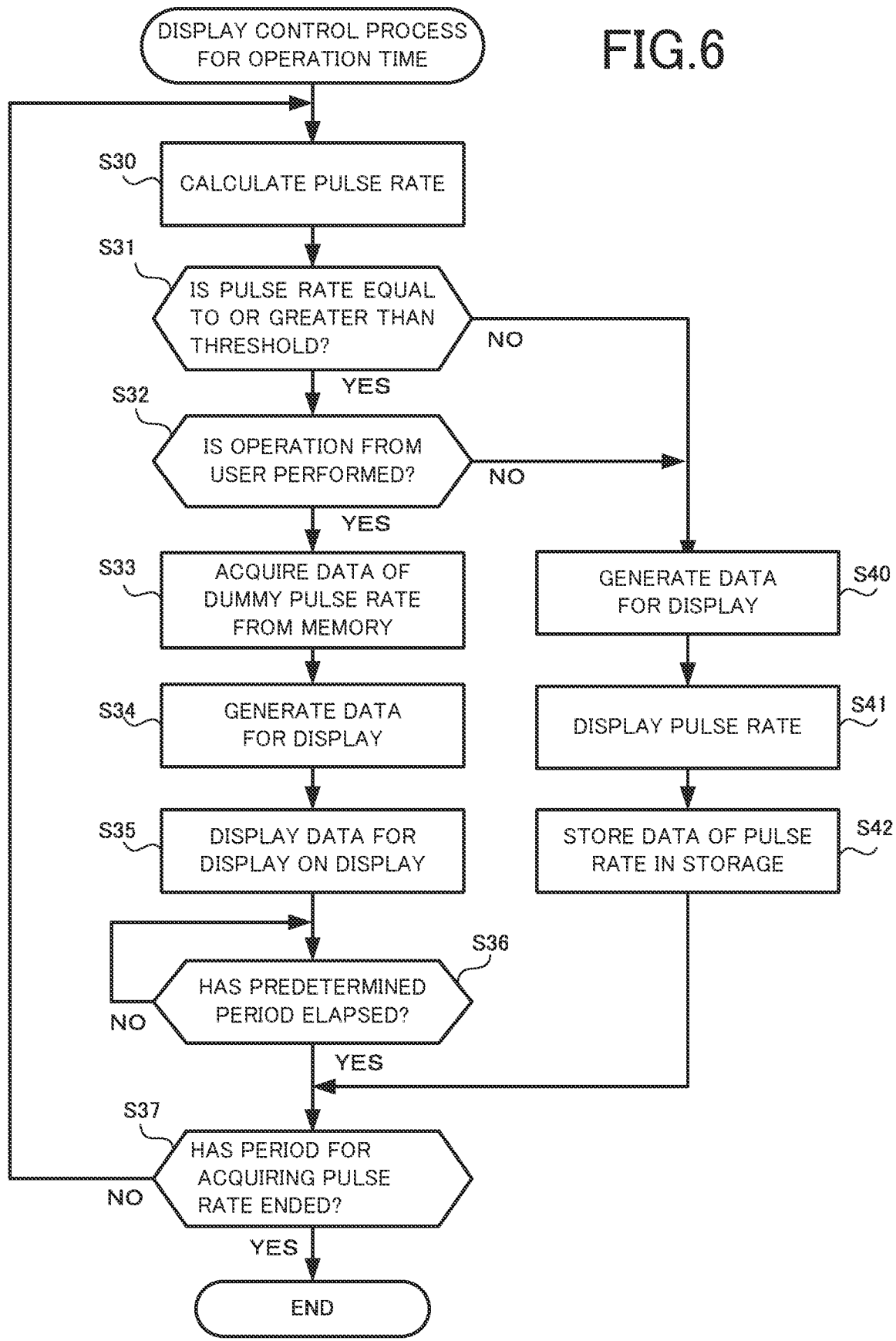
FIG. 6 is a flowchart illustrating a flow of a display control process for operation time, which is executed by an electronic device according to Embodiment 2.

An operation of a display control process for operation time in Embodiment 2 will be described with reference to a flowchart illustrated in FIG. 6. The display control process for operation time, like the display control process described in Embodiment 1, is stored as a display control process program for operation time in the storage 21 illustrated in FIG. 2. In the electronic device 100, when the function of measuring the pulse rate of the user and displaying the pulse rate is executed, the controller 25 illustrated in FIG. 2 reads out the display control process program for operation time from the storage 21, loads the display control process program for operation time in the RAM of the controller 25, and executes the display control process program for operation time.

The pulse data acquirer 251 of the controller 25 illustrated in FIG. 2 acquires pulse data of the user from the pulse sensor 19. The pulse data acquirer 251 calculates a pulse rate from the acquired pulse data (step S30). The determiner 254 of the controller 25 acquires the pulse rate of the user from the pulse data acquirer 251, and determines whether or not the pulse rate is equal to or greater than a threshold (step S31). When the pulse rate is equal to or greater than the threshold (step S31; YES), the operation information acquirer 253 of the controller 25 illustrated in FIG. 2 acquires data relating to an operation from the user in the operator 23. Here, for example, it is assumed that the user rotated the rotary bezel 11 illustrated in FIG. 1A.

The determiner 254 determines whether or not the data acquired from the operation information acquirer 253 is data indicating that an operation from the user was performed (step S32). When the determiner 254 determines that the data acquired from the operation information acquirer 253 is data indicating that an operation from the user was performed (step S32; YES), the display controller 255 acquires data of the pulse rate, which was stored immediately before and includes no error, from the storage 21, that is, data of a dummy pulse rate (step S33). Subsequently, the display controller 255 acquires set data for dummy display from the storage 21. The display controller 255 generates data for display, based on the data of the dummy pulse rate and the acquired set data for dummy display (step S34). For example, as illustrated in FIG. 4A, the display controller 255 generates data for display, which displays the specific mark 110 near the display of the pulse rate.

The display controller 255 causes the display 10 illustrated in FIG. 1 to display the generated data for display (step S35). The determiner 254 determines whether or not a predetermined period has elapsed since the data for display generated by the display controller 255 was displayed on the display 10 (step S36). The predetermined period is, for example, a period preset by the user. When the determiner 254 determines that the predetermined period has elapsed (step S36; YES), the determiner 254 determines whether a period for acquiring a pulse rate has terminated (step S37). For example, by an operation from the push button 13, 14 or the touch panel 10b illustrated in FIG. 1, when the screen is switched from the screen displaying both the present time and the pulse rate to the screen displaying only the present time, or when an instruction not to acquire the pulse rate is given, the determiner 254 can determine that the period for acquiring the pulse rate has ended. When the determiner 254 does not determine that the predetermined period has elapsed (step S36; NO), the determiner 254 repeats step S36.

When the determiner 254 determines that the period for acquiring the pulse rate has ended (step S37; YES), the controller 25 terminates the display control process program. On the other hand, when the determiner 254 does not determine that the period for acquiring the pulse rate has ended (step S37; NO), the controller 25 returns to step S30 and executes step S30 onwards.

In addition, if the determiner 254 determines in step S31 that the pulse rate, which is calculated from the pulse data acquired by the pulse data acquirer 251 of the controller 25, is not equal to or greater than the threshold (step S31; NO), or if the determiner 254 determines in step S32 that the data acquired from the operation information acquirer 253 is not data indicating that an operation from the user was performed (step S32; NO), the display controller 255 generates data for display, based on the pulse rate calculated from the pulse data of the user acquired from the pulse data acquirer 251 (step S40). The display controller 255 causes the display 10 illustrated in FIG. 1 to display the generated data for display (step S41). The pulse data acquirer 251 stores the pulse rate calculated from the pulse data acquired from the pulse sensor 19 in the storage 21 (step S42). The controller 25 executes step S37.

As described above, according to the electronic device 100 of Embodiment 2, an operation from the user on the operator 23 is detected. Thereby, in the electronic device 100 that is worn, the pulse rate including no error due to the operation of the user, that is, the biological information including no error, can be displayed. Hence, a great variation does not occur in the value of the biological information displayed on the display 10 of the electronic device 100, and the possibility that the user doubts whether the value of the displayed biological information is correct or not can be lowered.

Modifications

The present disclosure is not limited to Embodiments 1 and 2 described above, and, needless to say, various modifications can be made without departing from the spirit of the present disclosure.

In Embodiment 1, the determination as to whether or not to cause the display 10 of the electronic device 100 to display the dummy pulse rate is executed in accordance with the acceleration detected by the motion detection sensor 20, and, in Embodiment 2, this determination is executed according to whether or not the operation from the user was performed on the operator 23. Aside from this, the determination as to whether or not to cause the display 10 of the electronic device 100 to display the dummy pulse rate may be executed in accordance with the acceleration detected by the motion detection sensor 20, and/or according to whether or not the operation from the user was performed on the operator 23.

In Embodiments 1 and 2, it is assumed that the data of the pulse rate, which is stored in the storage 21 immediately before and includes no error, is used as the data of the dummy pulse rate. Aside from this, use may be made of an average value of the data of pulse rates which are stored in the storage 21 and include no error, or data of a dummy pulse rate stored in advance in the storage 21. Further, the next pulse rate may be estimated by calculating a differential value from the data of the pulse rate of the user, and the dummy pulse rate may be displayed. In addition, the number of dummy pulse rates is not limited to one, and, for example, a plurality of dummy pulse rates may be displayed, while being varied, in accordance with vibration occurring when the user is running.

In Embodiments 1 and 2, when the dummy pulse rate is displayed, a pulse rate that is measured in real time is not displayed. Both the pulse rate measured in real time and the dummy pulse rate may be displayed at the same time.

In Embodiments 1 and 2, when the dummy pulse rate is displayed, the data of the pulse rate continues to be acquired, but the data of the pulse rate may not be acquired at least during the period in which the dummy pulse rate is displayed.

In Embodiments 1 and 2, it is assumed that the pulse rate of the user is used as the biological information. Aside from this, various pieces of information detected from the user, such as the body temperature, blood pressure and brain wave, may be used as the biological information. In addition, in Embodiments 1 and 2, it is assumed that the pulse sensor 19 is used as biological information acquisition means. Aside from this, as the biological information acquisition means, a temperature sensor, a blood pressure measuring device, a brain wave measuring device, or the like may be used, in accordance with biological information to be acquired. Note that the biological information acquisition means, such as the pulse sensor 19, the temperature sensor, the blood pressure measuring device, or the brain wave measuring device, is an example of a biological information acquirer in the patent claims.

Furthermore, in Embodiments 1 and 2, it is assumed that the electronic device 100 is used the wearable terminal which can be worn on, for example, the wrist, arm or the like of the user. Aside from this, the wearable terminal may be changed in accordance with the kind of biological information to be acquired. For example, use may be made of terminals of various forms in accordance with biological information to be measured, such as an eyeglass-type terminal in the case of detecting the brain wave, or a finger-ring-type terminal in the case of measuring the body temperature.

In Embodiments 1 and 2, the determination as to whether or not to cause the display 10 of the electronic device 100 to display the dummy pulse rate is executed based on the data detected by the motion detection sensor 20 or the operator 23. Aside from this, the determination may be executed based on data detected from a solar panel, a geomagnetism sensor, a microphone, or the like.

In addition, methods of application of the display control process program and the display control process program for operation time in Embodiments 1 and 2 can be freely chosen. For example, each program can be applied by being stored in a computer-readable storage medium, such as a flexible disc, a compact disc (CD)-ROM, a digital versatile disc (DVD)-ROM, or a memory card. Further, a program can be superimposed on a carrier wave, and can be applied via a communication medium such as the Internet. For example, a program may be delivered by being posted on a bulletin board system (BBS) on a communication network. Besides, such a configuration may be adopted that the above-described process can be executed by starting and executing this program under the control of an operating system (OS), like other application programs.

The foregoing describes some example embodiments for explanatory purposes.

Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. An electronic device comprising:
   a biological information acquirer that acquires biological information of a target;
   an error factor detector that detects a factor that causes an error in the biological information;
   a display; and
   at least one processor, wherein
   the error factor detector includes a motion detection sensor that detects a direction of motion of the electronic device, and
   the processor
   determines whether the factor is detected, based on the direction of the motion of the electronic device; and
   causes, when the processor determines that the factor is detected, the display not to display the biological information acquired by the biological information acquirer, or causes the biological information acquirer to stop acquisition of the biological information, in a first period determined based on a timing when the factor is detected,
   causes, when the factor is detected, the display to display, in the first period, biological information that is based on the biological information acquired before the factor is detected;
   causes the display to display the biological information newly acquired by the biological information acquirer after the first period has ended and a user has not generated an instruction to end display or acquisition of the biological information; and
   causes the display to display the biological information newly acquired by the biological information acquirer, when the motion detection sensor detects that the electronic device moves in a direction opposite to a direction in which the electronic device moved at the timing when the factor was detected and the user has not generated an instruction to the processor to end display or acquisition of the biological information.

2. The electronic device according to claim 1, wherein the processor
causes the display to update display content, based on the biological information acquired by the biological information acquirer; and
causes, when the factor is not detected, the display to update the display content, based on at least the biological information which is not yet reflected in the display content.

3. The electronic device according to claim 1, wherein the biological information acquirer is a pulse sensor for acquiring a pulse of the target.

4. The electronic device according to claim 1, wherein the error factor detector includes an acceleration sensor, and
the processor determines that the factor is detected, when an acceleration detected by the acceleration sensor is equal to or greater than a threshold.

5. The electronic device according to claim 1, wherein the processor determines that the factor is detected, when the motion detection sensor detects that an acceleration in a certain direction is equal to or greater than a threshold.

6. The electronic device according to claim 1, wherein the error factor detector includes an operator, and
the processor determines that the factor is detected, when an operation was performed on the operator.

7. The electronic device according to claim 1, further comprising:
a memory that stores biological information acquired from the target, wherein
the processor causes the display to display, in the first period, data of the biological information stored in the memory before the timing when the factor is detected.

8. The electronic device according to claim 1, wherein the processor newly acquires, when the motion detection sensor does not detect that the electronic device moves in a direction opposite to a direction in which the electronic device moved at the timing when the factor was detected and the user has not generated an instruction to end display or acquisition of the biological information, the biological information by the biological information acquirer and causes the display to display the biological information.

9. A method executed in an electronic device, the method comprising:
acquiring biological information of a target;
detecting a direction of motion of the electronic device;
detecting a factor of an error included in the biological information;
displaying the biological information;
determining whether the factor is detected, based on the direction of the motion of the electronic device;
not displaying, when determining that the factor is detected, the biological information, or stopping acquisition of the biological information, in a first period determined based on a timing when the factor is detected;
displaying, when the factor is detected, in the first period, biological information that is based on biological information acquired before the factor is detected;
newly acquiring the biological information and displaying the newly acquired biological information after the first period has ended and a user has not generated an instruction to end display or acquisition of the biological information; and
newly acquiring the biological information and displaying the newly acquired biological information when the detected direction of motion of the electronic device is in a direction opposite to the direction in which the electronic device moved at the timing when the factor was detected and the user has not generated an instruction to end display or acquisition of the biological information.

10. A storage medium for storing a program for causing at least one processor to execute:
a process of acquiring biological information of a target;
a process of detecting a direction of motion of the electronic device;
a process of detecting a factor of an error included in the biological information;
a process of displaying the biological information;
a process of determining whether the factor is detected, based on the direction of the motion of the electronic device;
a process of not displaying, when determining that the factor is detected, the biological information, or a process of stopping acquisition of the biological information, in a first period determined based on a timing when the factor is detected;
a process of displaying, when the factor is detected, in the first period, biological information that is based on biological information acquired before the factor is detected;
a process of newly acquiring the biological information and displaying the newly acquired biological information after the first period has ended and a user has not generated an instruction to end display or acquisition of the biological information; and
a process of newly acquiring the biological information and displaying the newly acquired biological information when the detected direction of motion of the electronic device is in a direction opposite to the direction in which the electronic device moved at the timing when the factor was detected and the user has not generated an instruction to end display or acquisition of the biological information.

* * * * *